(12) United States Patent
Cantrell et al.

(10) Patent No.: US 8,563,727 B2
(45) Date of Patent: Oct. 22, 2013

(54) (+)-MORPHINANIUM N-OXIDES AND PROCESSES FOR THEIR PRODUCTION

(75) Inventors: Gary L. Cantrell, Troy, IL (US); Peter X. Wang, Clarkson Valley, MO (US); Bobby N. Trawick, Florissant, MO (US); Christopher W. Grote, Webster Groves, MO (US); David W. Berberich, St. Peters, MO (US); Hang Sun, Chesterfield, MO (US); Subo Liao, Ballwin, MO (US)

(73) Assignee: Mallinckrodt LLC, Hazelwood, MO (US)

( * ) Notice: Subject to any disclaimer, the term of this patent is extended or adjusted under 35 U.S.C. 154(b) by 563 days.

(21) Appl. No.: 12/710,383

(22) Filed: Feb. 23, 2010

(65) Prior Publication Data

US 2010/0216997 A1 Aug. 26, 2010

Related U.S. Application Data

(60) Provisional application No. 61/154,451, filed on Feb. 23, 2009.

(51) Int. Cl.
*C07D 221/28* (2006.01)

(52) U.S. Cl.
USPC .......................................................... 546/75

(58) Field of Classification Search
USPC .................................................... 546/44, 75
See application file for complete search history.

(56) References Cited

U.S. PATENT DOCUMENTS

| | | |
|---|---|---|
| 5,739,145 A | 4/1998 | Nagase et al. |
| 6,174,891 B1 | 1/2001 | Nagase et al. |
| 6,277,859 B1 | 8/2001 | Nagase et al. |
| 2004/0077863 A1 | 4/2004 | Scammells et al. |
| 2004/0204434 A1 | 10/2004 | Shafer et al. |
| 2005/0182258 A1 | 8/2005 | Schmidhammer et al. |
| 2007/0265293 A1 | 11/2007 | Boyd et al. |
| 2008/0161570 A1 | 7/2008 | Perez et al. |
| 2008/0176884 A1 | 7/2008 | Perez et al. |
| 2008/0207669 A1 | 8/2008 | Perez et al. |
| 2008/0214817 A1 | 9/2008 | Dlubala |
| 2008/0234306 A1 | 9/2008 | Perez et al. |
| 2008/0274119 A1 | 11/2008 | Moss et al. |
| 2009/0062544 A1 | 3/2009 | Wakita et al. |

FOREIGN PATENT DOCUMENTS

| | | |
|---|---|---|
| CH | 683 005 A5 | 12/1993 |
| DE | 1119284 | 12/1961 |
| EP | 0 418 591 | 3/1991 |
| JP | 2001-302668 | 10/2001 |
| WO | WO 01/14382 | 3/2001 |
| WO | WO 01/74819 | 4/2001 |
| WO | WO 2004/043964 | 5/2004 |
| WO | WO 2005/028483 | 3/2005 |
| WO | WO 2006/096626 | 9/2006 |
| WO | WO 2006/127899 | 11/2006 |

OTHER PUBLICATIONS

Kelentey et al., "Preparation and pharmacological properties of n-oxides of opium alkaloids", Kiserletes orvostudomany, 1958, 10(1), pp. 70-77.
Kelentey et al., "Preparation and pharmacological studies of n-oxides of opium alkaloids", Arzneimittel-Forschung, 1957, 7, pp. 594-597.
Takagi et al., "Antitussive Activity of the N-Oxides of Opium Alkaloids", Journal of the Pharmaceutical Society of Japan, 77(11), 1957 p. 1358.
Takagi et al., "Studies on Antitussives. II. Opium Alkaloids and their N-Oxides", Journal of the Pharmaceutical Socie of Japan, 80(10), 1960, pp. 1501-1506.
Heumans et al., "Some aspects of the metabolism of morphine-$N$-oxide", J. Pharm. Pharmac., 1971, 23, pp. 831-836.
Bao et al., "Morphinane Alkaloids with Cell Protective Effects from *Sinomenium acutum*", J. Nat. Prod., 2005, 68, pp. 1128-1130.
Makareviche et al., "Quaternary Salts of Alkaloids", Chemistry of Natural Compounds, 2006, 42(4), pp. 473-476.

*Primary Examiner* — Shawquia Young

(57) ABSTRACT

The present invention provides (+)-morphinanium N-oxide compounds or pharmaceutically acceptable salts thereof. The invention also provides processes for producing (+)-morphinanium N-oxides or pharmaceutically acceptable salts thereof from the corresponding tertiary N-substituted (+)-morphinan compound or pharmaceutically acceptable salt thereof.

9 Claims, No Drawings

(+)-MORPHINANIUM N-OXIDES AND PROCESSES FOR THEIR PRODUCTION

CROSS REFERENCE TO RELATED APPLICATIONS

This application claims priority from U.S. Provisional Application No. 61/154,451 filed on Feb. 23, 2009, which is hereby incorporated by reference in its entirety.

FIELD OF THE INVENTION

The present invention generally relates to (+)-morphinanium N-oxides. In particular, the present invention provides (+)-morphinanium N-oxide compounds and processes for producing (+)-morphinanium N-oxides form the corresponding tertiary N-substituted (+)-morphinan compounds.

BACKGROUND OF THE INVENTION

Opioids are a group of drugs that exhibit opium or morphine-like properties. They are employed primarily as moderate to strong analgesics, but have many other pharmacological effects as well, including drowsiness, respiratory depression, constipation, changes in mood, and mental clouding without a resulting loss of consciousness. Morphine and codeine are by far the most important naturally occurring opiate agonists. Substitution of the nitrogen atom of the morphinan ring of these compounds affects their pharmacologic properties. For example, morphinan derivatives having various nitrogen substituents exhibit partial agonist/antagonist activity or potent antagonist activity. Morphinan compounds comprising quaternary amines are also known. For example, N-oxides of certain morphinans have been variously reported to be less active than the corresponding tertiary amine.

Recent research has shown that morphinans comprising opiate receptor antagonists and; in particular, their respective quaternary amines are potent inhibitors of vascular endothelial growth factor (VEGF). VEGF inhibitors are important adjuncts in the treatment of various tumors and the treatment of macular degeneration. More recent work has suggested that VEGF inhibitory activity appears to be independent of the stereochemistry of the morphinan ring system. That is, (+)-morphinan quaternary compounds appear to inhibit VEGF as well as the pharmacologically active (−)-morphinan quaternary compounds. Thus, other (+)-morphinan derivatives such as (+)-morphinanium N-oxides may be useful as improved VEGF inhibitors because they do not interact with opiate receptors. There is a need, therefore, for processes for synthesizing (+)-morphinanium N-oxides.

SUMMARY OF THE INVENTION

The present invention provides (+)-morphinanium N-oxide compounds or pharmaceutically acceptable salts thereof. The present invention also provides synthetic processes for the production of (+)-morphinanium N-oxides or pharmaceutically acceptable salts thereof from the corresponding tertiary N-substituted (+)-morphinan compounds or pharmaceutically acceptable salts thereof.

One aspect of the present invention encompasses a compound comprising Formula (II) or a pharmaceutically acceptable salt thereof:

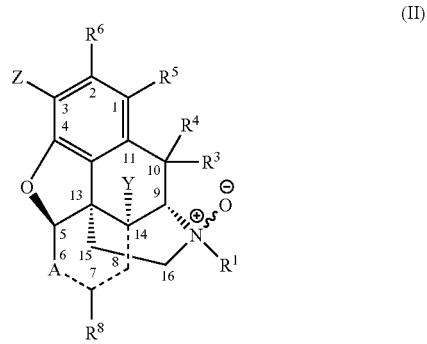

(II)

wherein:

A is selected from the group consisting of {—}C(O){—}, {—}C(=CH$_2$){—}, {—}CH$_2${—}, {—}CH(A$^1$){—}, and

{—}C(A$^1$){=};

A$^1$ is selected from the group consisting of hydroxy, alkoxy, acyloxy, amido, hydrocarbyl, and substituted hydrocarbyl;

R$^1$ and R$^7$ are independently selected from the group consisting of hydrocarbyl and substituted hydrocarbyl;

R$^3$ and R$^4$ are independently selected from the group consisting of hydrogen, hydrocarbyl and substituted hydrocarbyl;

R$^5$ and R$^6$ are independently selected from the group consisting of hydrogen, hydrocarbyl, substituted hydrocarbyl, halogen, {—}OH, and {—}OR$^7$;

R$^8$ is selected from the group consisting of hydrogen, hydrocarbyl, and substituted hydrocarbyl;

Y, if present, is selected from the group consisting of hydrogen, hydroxy, protected hydroxy, alkoxy, and acyloxy;

Z is selected from the group consisting of hydroxy, protected hydroxy, alkoxy, and acyloxy; and the dashed lines between the carbon atoms at positions 6 and 7, 7 and 8, and 8 and 14 represent carbon to carbon bonds selected from the group consisting of (a) single bonds between all carbon atoms, wherein the carbons at positions 6 and 14 may be connected by an alkano bridge; (b) single bonds between the carbons at both positions 6 and 7 and 8 and 14, and a double bond between the carbons at positions 7 and 8; and (c) double bonds between the carbons at both positions 6 and 7 and 8 and 14, and a single bond between the carbons at positions 7 and 8, wherein Y is not present if there is a double bond between the carbons at positions 8 and 14.

Another aspect of the invention provides a compound comprising Formula (IV) or a pharmaceutically acceptable salt thereof:

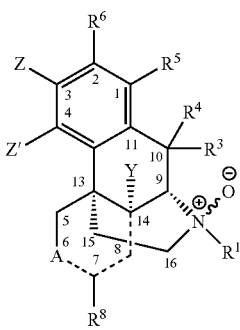

(IV)

wherein:
A is selected from the group consisting of {—}C(O){—}, {—}C(=CH₂){—}, {—}CH₂{—}, {—}CH(A¹){—}, and
{—}(A¹){=};
A¹ is selected from the group consisting of hydroxy, alkoxy, acyloxy, amido, hydrocarbyl, and substituted hydrocarbyl;
R¹ and R⁷ are independently selected from the group consisting of hydrocarbyl and substituted hydrocarbyl;
R³ and R⁴ are independently selected from the group consisting of hydrogen, hydrocarbyl, and substituted hydrocarbyl;
R⁵ and R⁶ are independently selected from the group consisting of hydrogen, hydrocarbyl, substituted hydrocarbyl, halogen, {—}OH, and {—}OR⁷;
R⁸ is selected from the group consisting of hydrogen, hydrocarbyl, and substituted hydrocarbyl;
Y, if present, is selected from the group consisting of hydrogen, hydroxy, protected hydroxy, alkoxy, and acyloxy;
Z is selected from the group consisting of hydroxy, protected hydroxy, alkoxy, and acyloxy;
Z' is selected from the group consisting of hydrogen, hydroxy, protected hydroxy, alkoxy, and acyloxy; and
the dashed lines between the carbon atoms at positions 6 and 7, 7 and 8, and 8 and 14 represent carbon to carbon bonds selected from the group consisting of (a) single bonds between all carbon atoms; (b) single bonds between the carbons at both positions 6 and 7 and 8 and 14, and a double bond between the carbons at positions 7 and 8, wherein A is not {—}C(O){—} if there is a double bond between the carbons at positions 7 and 8; and (c) double bonds between the carbons at both positions 6 and 7 and 8 and 14, and a single bond between the carbons at positions 7 and 8, wherein Y is not present if there is a double bond between the carbons at positions 8 and 14.

Still another aspect of the invention encompasses a process for the preparation of a (+)-morphinanium N-oxide or a pharmaceutically acceptable salt thereof. The process comprises contacting a (+)-morphinan comprising a tertiary amine at position 17 or a pharmaceutically acceptable salt thereof with an oxidizing agent to form the (+)-morphinanium N-oxide comprising a quaternary amine at position 17 or the pharmaceutically acceptable salt thereof.

A further aspect of the invention provides a process for the preparation of a compound comprising Formula (II) or a pharmaceutically acceptable salt thereof. The process comprises contacting a compound comprising Formula (I) or a pharmaceutically acceptable salt thereof with an oxidizing agent to form the compound comprising Formula (II) or a pharmaceutically acceptable salt thereof according to the following reaction:

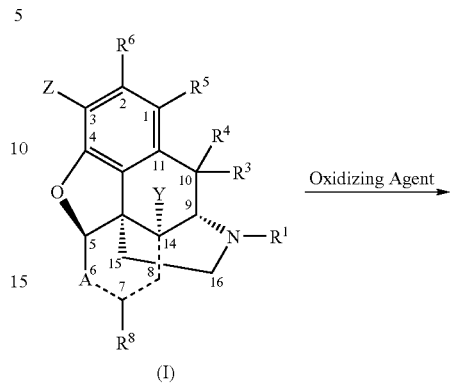

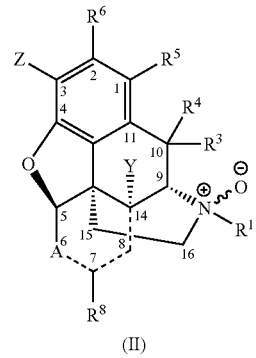

(II)

wherein:
A is selected from the group consisting of {—}C(O){—}, {—}C(=CH₂){—}, {—}CH₂{—}, {—}CH(A¹){—}, and
{—}C(A¹){=};
A¹ is selected from the group consisting of hydroxy, alkoxy, acyloxy, amido, hydrocarbyl, and substituted hydrocarbyl;
R¹ and R⁷ are independently selected from the group consisting of hydrocarbyl and substituted hydrocarbyl;
R³ and R⁴ are independently selected from the group consisting of hydrogen, hydrocarbyl and substituted hydrocarbyl;
R⁵ and R⁶ are independently selected from the group consisting of hydrogen, hydrocarbyl, substituted hydrocarbyl, halogen, {—}OH, and {—}OR⁷;
R⁸ is selected from the group consisting of hydrogen, hydrocarbyl, and substituted hydrocarbyl;
Y, if present, is selected from the group consisting of hydrogen, hydroxy, protected hydroxy, alkoxy, and acyloxy;
Z is selected from the group consisting of hydroxy, protected hydroxy, alkoxy, and acyloxy; and
the dashed lines between the carbon atoms at positions 6 and 7, 7 and 8, and 8 and 14 represent carbon to carbon bonds selected from the group consisting of (a) single bonds between all carbon atoms, wherein the carbons at positions 6 and 14 may be connected by an alkano bridge; (b) single bonds between the carbons at both positions 6 and 7 and 8 and 14, and a double bond between the carbons at positions 7 and 8; and (c) double bonds between the carbons at both positions 6 and 7 and 8 and 14, and a single bond between the carbons at positions 7 and 8, wherein Y is not present if there is a double bond between the carbons at positions 8 and 14.

Yet another aspect of the present invention encompasses a process for the preparation of a compound comprising Formula (IV) or a pharmaceutically acceptable salt thereof. The process comprises contacting a compound comprising Formula (III) or a pharmaceutically acceptable salt thereof with an oxidizing agent to form the compound comprising Formula (IV) or a pharmaceutically

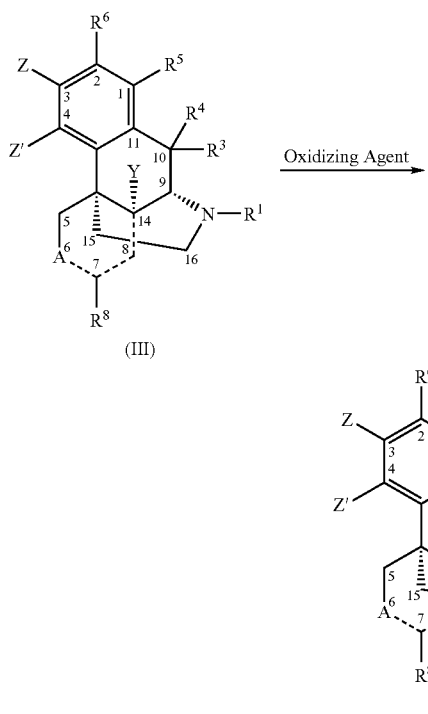

acceptable salt thereof according to the following reaction: wherein:

A is selected from the group consisting of {—}C(O){—}, {—}C(=CH$_2$){—}, {—}CH$_2${—}, {—}CH(A$^1$){—}, and {—}C(A$^1$){=};

A$^1$ is selected from the group consisting of hydroxy, alkoxy, acyloxy, amido, hydrocarbyl, and substituted hydrocarbyl;

R$^1$ and R$^7$ are independently selected from the group consisting of hydrocarbyl and substituted hydrocarbyl;

R$^3$ and R$^4$ are independently selected from the group consisting of hydrogen, hydrocarbyl, and substituted hydrocarbyl;

R$^5$ and R$^6$ are independently selected from the group consisting of hydrogen, hydrocarbyl, substituted hydrocarbyl, halogen, {—}OH, and {—}OR$^7$;

R$^8$ is selected from the group consisting of hydrogen, hydrocarbyl, and substituted hydrocarbyl;

Y, if present, is selected from the group consisting of hydrogen, hydroxy, protected hydroxy, alkoxy, and acyloxy;

Z is selected from the group consisting of hydroxy, protected hydroxy, alkoxy, and acyloxy;

Z' is selected from the group consisting of hydrogen, hydroxy, protected hydroxy, alkoxy, and acyloxy; and the dashed lines between the carbon atoms at positions 6 and 7, 7 and 8, and 8 and 14 represent carbon to carbon bonds selected from the group consisting of (a) single bonds between all carbon atoms; (b) single bonds between the carbons at both positions 6 and 7 and 8 and 14, and a double bond between the carbons at positions 7 and 8; and (c) double bonds between the carbons at both positions 6 and 7 and 8 and 14, and a single bond between the carbons at positions 7 and 8, wherein Y is not present if there is a double bond between the carbons at positions 8 and 14.

Other aspects and iterations of the invention are described in more detail below.

DETAILED DESCRIPTION OF THE INVENTION

The present invention provides (+)-morphinanium N-oxide compounds that may be useful as VEGF inhibitors. The present invention also provides processes for the production (+)-morphinanium N-oxide compounds or pharmaceutically acceptable salts thereof. The process utilizes a direct N-oxidation of a tertiary amine of a (+)-morphinan compound or a pharmaceutically acceptable salt thereof into a (+)-morphinanium N-oxide or a pharmaceutically acceptable salt thereof comprising a quaternary amine. In particular, the process comprises contacting the (+)-morphinan compound or the pharmaceutically acceptable salt thereof with an oxidizing agent.

(I) (+)-Morphinanium N-Oxides (a) Compounds Comprising Formula (II)

One aspect of the present invention encompasses a (+)-morphinanium N-oxide compound or a pharmaceutically acceptable salt thereof comprising a quaternary amine. In one embodiment, the compound comprises Formula (II) or a pharmaceutically acceptable salt thereof:

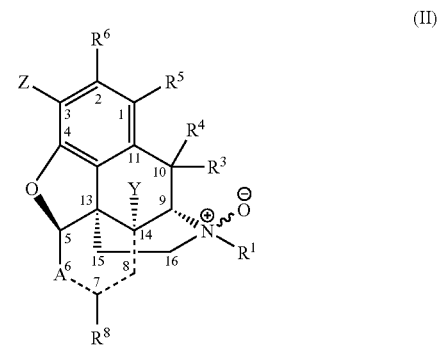

wherein:

A is selected from the group consisting of {—}C(O){—}, {—}C(=CH$_2$){—}, {—}CH$_2${—}, {—}CH(A$^1$){—}, and {—}C(A$^1$){=};

A$^1$ is selected from the group consisting of hydroxy, alkoxy, acyloxy, amido, hydrocarbyl, and substituted hydrocarbyl;

R$^1$ and R$^7$ are independently selected from the group consisting of hydrocarbyl and substituted hydrocarbyl;

R$^3$ and R$^4$ are independently selected from the group consisting of hydrogen, hydrocarbyl and substituted hydrocarbyl;

R$^5$ and R$^6$ are independently selected from the group consisting of hydrogen, hydrocarbyl, substituted hydrocarbyl, halogen, {—}OH, and {—}OR$^7$;

R⁸ is selected from the group consisting of hydrogen, hydrocarbyl, and substituted hydrocarbyl;

Y, if present, is selected from the group consisting of hydrogen, hydroxy, protected hydroxy, alkoxy, and acyloxy;

Z is selected from the group consisting of hydroxy, protected hydroxy, alkoxy, and acyloxy; and the dashed lines between the carbon atoms at positions 6 and 7, 7 and 8, and 8 and 14 represent carbon to carbon bonds selected from the group consisting of (a) single bonds between all carbon atoms, wherein the carbons at positions 6 and 14 may be connected by an alkano bridge; (b) single bonds between the carbons at both positions 6 and 7 and 8 and 14, and a double bond between the carbons at positions 7 and 8; and (c) double bonds between the carbons at both positions 6 and 7 and 8 and 14, and a single bond between the carbons at positions 7 and 8, wherein Y is not present if there is a double bond between the carbons at positions 8 and 14.

As used herein, the term "substituted hydrocarbyl" refers to a hydrocarbyl moiety that is substituted with at least one heteroatom, including moieties in which a carbon chain atom is substituted with a heteroatom, provided that the heteroatom does not react with an oxidizing agent, as defined herein.

In preferred iterations, $R^3$, $R^4$, $R^5$, and $R^6$ are each hydrogen. $R^1$ is preferably alkyl, cycloalkyl, cycloalkylmethyl, allyl, or aryl; or more preferably methyl, ethyl, propyl, allyl, cyclopropylmethyl, cyclobutylmethyl, benzyl, or propargyl.

In one iteration of this embodiment, the compound comprises Formula (IIa) or a pharmaceutically acceptable salt thereof:

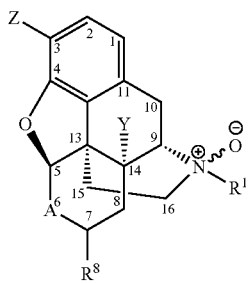

(IIa)

wherein:

A is selected from the group consisting of {—}C(O){—}, {—}C(=CH₂){—}, {—}CH₂{—}, and {—}(CH(A¹){—}, wherein the carbons at positions 6 and 14 may be connected by an alkano bridge;

A¹ is selected from the group consisting of hydroxy, alkoxy, acyloxy, amido, hydrocarbyl, and substituted hydrocarbyl;

R¹ is selected from the group consisting of hydrocarbyl and substituted hydrocarbyl;

R⁸ is selected from the group consisting of hydrogen, hydroxy, alkyl, substituted alkyl, alkoxy, hydrocarbyl, and substituted hydrocarbyl;

Y is selected from the group consisting of hydrogen, hydroxy, alkoxy, and acyloxy; and Z is selected from the group consisting of hydroxy, alkoxy, and acyloxy.

Representative compounds comprising Formula (IIa) or pharmaceutically acceptable salts thereof include N-oxides of (+)-dihydromorphine, (+)-dihydrocodeine, (+)-hydrocodone, (+)-hydromorphone, (+)-oxycodone, (+)-oxycodeinone, (+)-oxymorphone, (+)-naloxone, (+)-naltrexone, (+)-nalbuphine, (+)-nalfurafine, (+)-nalmefene, (+)-buprenorphine, and (+)-etorphine.

In another iteration of this embodiment, the compound comprises Formula (IIb) or a

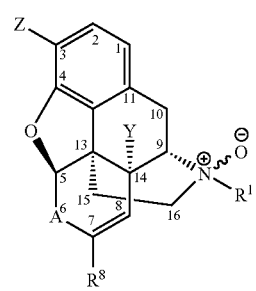

(IIb)

pharmaceutically acceptable salt thereof:

wherein:

A is selected from the group consisting of {—}C(O){—}, {—}C(=CH₂){—}, {—}CH₂{—}, and {—}(CH(A¹){—}; and A¹, R¹, R⁸, Y, and Z are as defined above for compounds comprising Formula (IIa).

Representative compounds comprising Formula (IIb) or pharmaceutically acceptable salts thereof include N-oxides of (+)-morphine, (+)-codeine, and (+)-morphine-6-glucoronide.

In still another iteration of this embodiment, the compound comprises Formula (IIc) or a pharmaceutically acceptable salt thereof:

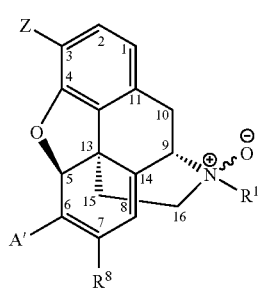

(IIc)

wherein:

A¹, R¹, R⁸, and Z are as defined above for compounds comprising Formula (IIa).

Representative compounds comprising Formula (IIb) or pharmaceutically acceptable salts thereof include N-oxides of (+)-thebaine and (+)-oripavine.

(b) Compounds Comprising Formula (IV)

In another embodiment of the invention, the (+)-morphinanium quaternary N-oxide compound comprises Formula (IV) or a pharmaceutically acceptable salt thereof:

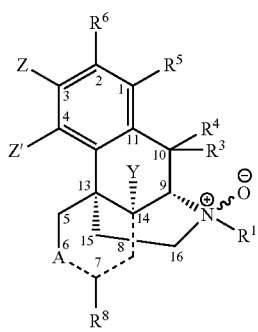

(IV)

wherein:
A is selected from the group consisting of {—}C(O){—}, {—}C(=CH$_2$){—}, {—}CH$_2${—}, {—}CH(A$^1$){—}, and {—}C(A$^1$){=};

A$^1$ is selected from the group consisting of hydroxy, alkoxy, acyloxy, amido, hydrocarbyl, and substituted hydrocarbyl;

R$^1$ and R$^7$ are independently selected from the group consisting of hydrocarbyl and substituted hydrocarbyl;

R$^3$ and R$^4$ are independently selected from the group consisting of hydrogen, hydrocarbyl, and substituted hydrocarbyl;

R$^5$ and R$^6$ are independently selected from the group consisting of hydrogen, hydrocarbyl, substituted hydrocarbyl, halogen, {—}OH, and {—}OR$^7$;

R$^8$ is selected from the group consisting of hydrogen, hydrocarbyl, and substituted hydrocarbyl;

Y, if present, is selected from the group consisting of hydrogen, hydroxy, protected hydroxy, alkoxy, and acyloxy;

Z is selected from the group consisting of hydroxy, protected hydroxy, alkoxy, and acyloxy;

Z' is selected from the group consisting of hydrogen, hydroxy, protected hydroxy, alkoxy, and acyloxy; and the dashed lines between the carbon atoms at positions 6 and 7, 7 and 8, and 8 and 14 represent carbon to carbon bonds selected from the group consisting of (a) single bonds between all carbon atoms; (b) single bonds between the carbons at both positions 6 and 7 and 8 and 14, and a double bond between the carbons at positions 7 and 8, wherein A is not {—}C(O){—} if there is a double bond between the carbons at positions 7 and 8; and (c) double bonds between the carbons at both positions 6 and 7 and 8 and 14, and a single bond between the carbons at positions 7 and 8, wherein Y is not present if there is a double bond between the carbons at positions 8 and 14.

As used herein, the term "substituted hydrocarbyl" refers to a hydrocarbyl moiety that is substituted with at least one heteroatom, including moieties in which a carbon chain atom is substituted with a heteroatom, provided that the heteroatom does not react with an oxidizing agent, as defined herein.

In preferred iterations, R$^3$, R$^4$, R$^5$, and R$^6$ are each hydrogen. R$^1$ is preferably alkyl, cycloalkyl, cycloalkylmethyl, allyl, or aryl; or more preferably methyl, ethyl, propyl, allyl, cyclopropylmethyl, cyclobutylmethyl, benzyl, or propargyl.

In one iteration of this embodiment, the compound comprises Formula (IVa) or a pharmaceutically acceptable salt thereof:

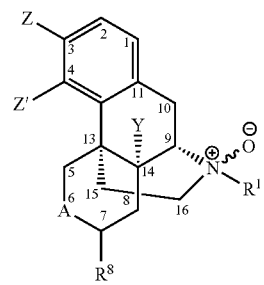

(IVa)

wherein:
A is selected from the group consisting of {—}C(O){—}, {—}C(=CH$_2$){—}, {—}CH$_2${—}, and {—}CH(A$^1$){—};

A$^1$ is selected from the group consisting of hydroxy, alkoxy, acyloxy, amido, hydrocarbyl, and substituted hydrocarbyl;

R$^1$ is selected from the group consisting of hydrocarbyl and substituted hydrocarbyl;

R$^8$ is selected from the group consisting of hydrogen, hydroxy, alkyl, substituted alkyl, alkoxy, hydrocarbyl, and substituted hydrocarbyl;

Y is selected from the group consisting of hydrogen, hydroxy, protected hydroxy, alkoxy, and acyloxy;

Z is selected from the group consisting of hydroxy, protected hydroxy, alkoxy, and acyloxy; and Z' is selected from the group consisting of hydrogen, hydroxy, protected hydroxy, alkoxy, and acyloxy.

Representative compounds comprising Formula (IVa) or pharmaceutically acceptable salts thereof include N-oxides of (+)-dextrorphan, (+)-dextromethorphan, and (+)-dihydrosinomenine.

In yet another iteration of this embodiment, the compound comprises Formula (IVb) or a pharmaceutically acceptable salt thereof:

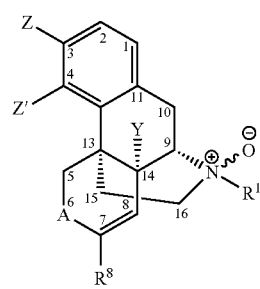

(IVb)

wherein:
A is selected from the group consisting of {—}C(=CH$_2$){—}, {—}CH$_2${—}, and {—}CH(A$^1$){—}; and A$^1$, R$^1$, R$^8$, Y, Z, and Z' are as defined above for compounds comprising Formula (IVa).

In still another iteration of this embodiment, the compound comprises Formula (IVc) or a pharmaceutically acceptable salt thereof:

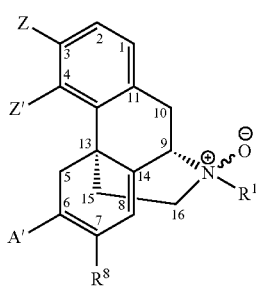

(IVc)

wherein:
A¹, R¹, R⁸, Y, Z, and Z' are as defined above for compounds comprising Formula (IVa).

The compounds comprising Formulas (II), (IIa), (IIb), (IIc), (IV), (IVa), (IVc), and pharmaceutically acceptable salts thereof all have a (+) orientation with respect to the rotation of polarized light. More specifically, each chiral center has an R or an S configuration. In particular, the carbon at position 5, if chiral, has an S configuration, the carbon at position 13 has an R configuration, the carbon at position 14, if chiral, has an R configuration, and the carbon at position 9 has an S configuration. In each of the compounds of the invention, the nitrogen at position 17 may comprise an R or an S configuration. In some embodiments, the compound of the invention may comprise a chiral carbon at position 6, and its configuration may be R or S. In other embodiments, the compound of the invention may comprise a chiral carbon at position 7, and its configuration may be R or S.

In each of these embodiments, pharmaceutically acceptable salts include without limitation hydrochloride, hydrobromide, phosphate, sulfate, methanesulfonate, acetate, formate, tartaric acid, bitartrate, stearate, phthalate, hydroiodide, lactate, monohydrate, mucate, nitrate, phosphate, salicylate, phenylpriopionate, isobutyrate, hypophosphite, maleic, malic, citrate, isocitrate, succinate, lactate, gluconate, glucuronate, pyruvate, oxalate, fumarate, propionate, aspartate, glutamate, benzoate, terephthalate, and the like.

Accordingly, the invention encompasses N-oxides of (+)-morphinan compounds including, but are not limited to, (+)-morphine sulfate, (+)-morphine hydrochloride, (+)-morphine acetate, (+)-morphine citrate, (+)-morphine bitartrate, (+)-morphine stearate, (+)-morphine phthalate, (+)-morphine hydrobromide, (+)-morphine hydroiodide, (+)-morphine lactate, (+)-morphine monohydrate, (+)-morphine nitrate, (+)-morphine phosphate, (+)-morphine salicylate, (+)-morphine phenylpropionate, (+)-morphine methyliodide, (+)-morphine isobutyrate, (+)-dihydromorphine hydrochloride, (+)-dihydromorphine hydroiodide, (+)-dihydromorphine monohydrate, (+)-ethylmorphine hydrochloride, (+)-codeine phosphate, (+)-codeine sulfate, (+)-codeine hydrochloride, (+)-codeine citrate, (+)-codeine salicylate, (+)-dihydrocodeine bitartrate, (+)-dihydrocodeine hydroiodide, (+)-dihydrocodeine tartrate, (+)-dihydrocodeine phosphate, (+)-dihydrocodeine hydrochloride, (+)-dihydrocodeine sulfate, (+)-hydrocodone bitartrate, (+)-hydrocodone tartrate, (+)-hydromorphone hydrochloride, (+)-hydromorphone sulfate, (+)-hydromorphone terephthalate, (+)-hydromorphone bitartrate, (+)-hydromorphone tartrate, (+)-hydromorphone hydroiodide, (+)-oxycodone hydrochloride, (+)-oxycodone tartrate, (+)-oxymorphone hydrochloride, (+)-thebaine, (+)-oripavine, (+)-naloxone hydrochloride, (+)-naltrexone hydrochloride, (+)-nalbuphine hydrochloride, (+)-nalfurafine, (+)-nalmefene hydrochloride, (+)-etorphine hydrochloride, (+)-morphine-G-glucuronide, (+)-noroxymorphone, (+)-buprenorphine hydrochloride, and the like.

(II) Synthesis of (+)-Morphinanium N-Oxides

Another aspect of the invention provides a process for the production of a (+)-morphinanium N-oxide or a pharmaceutically acceptable salt thereof. The process comprises a direct N-oxidation of a (+)-morphinan compound comprising a tertiary amine to produce a (+)-morphinanium N-oxide compound comprising a quaternary amine. In particular, the process comprises contacting a tertiary (+)-morphinan compound or a pharmaceutically acceptable salt thereof with an oxidizing agent such that a quaternary (+)-morphinanium N-oxide or a pharmaceutically acceptable salt thereof is produced.

(a) Synthesis of Compound Comprising Formula (II)

In one embodiment of the invention, a (+)-morphinanium N-oxide compound comprising Formula (II) or a pharmaceutically acceptable salt thereof is produced by reaction of a (+)-morphinan compound comprising Formula (I) or a pharmaceutically acceptable salt thereof with an oxidizing agent. For purposes of illustration, Reaction Scheme 1 depicts production of a (+)-morphinanium N-oxide compound comprising Formula (II) or a pharmaceutically acceptable salt thereof in accordance with one aspect of the invention:

Reaction Scheme 1

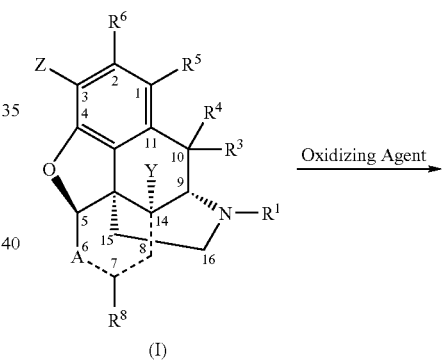

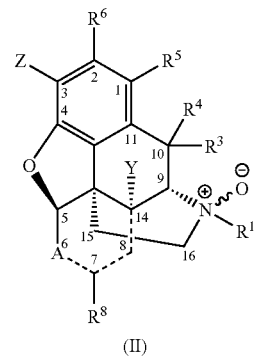

wherein:
A is selected from the group consisting of {—}C(O){—}, {—}C(=CH₂){—}, {—}CH₂{—}, {—}CH(A¹){—}, and
{—}C(A¹){=};
A¹ is selected from the group consisting of hydroxy, alkoxy, acyloxy, amido, hydrocarbyl, and substituted hydrocarbyl;

R[1] and R[7] are independently selected from the group consisting of hydrocarbyl and substituted hydrocarbyl;

R[3] and R[4] are independently selected from the group consisting of hydrogen, hydrocarbyl and substituted hydrocarbyl;

R[5] and R[6] are independently selected from the group consisting of hydrogen, hydrocarbyl, substituted hydrocarbyl, halogen, {—}OH, and {—}OR[7];

R[8] is selected from the group consisting of hydrogen, hydrocarbyl, and substituted hydrocarbyl;

Y, if present, is selected from the group consisting of hydrogen, hydroxy, protected hydroxy, alkoxy, and acyloxy;

Z is selected from the group consisting of hydroxy, protected hydroxy, alkoxy, and acyloxy; and the dashed lines between the carbon atoms at positions 6 and 7, 7 and 8, and 8 and 14 represent carbon to carbon bonds selected from the group consisting of (a) single bonds between all carbon atoms, wherein the carbons at positions 6 and 14 may be connected by an alkano bridge; (b) single bonds between the carbons at both positions 6 and 7 and 8 and 14, and a double bond between the carbons at positions 7 and 8; and (c) double bonds between the carbons at both positions 6 and 7 and 8 and 14, and a single bond between the carbons at positions 7 and 8, wherein Y is not present if there is a double bond between the carbons at positions 8 and 14.

As used herein, the term "substituted hydrocarbyl" refers to a hydrocarbyl moiety that is substituted with at least one heteroatom, including moieties in which a carbon chain atom is substituted with a heteroatom, provided that the heteroatom does not react with an oxidizing agent, as defined herein.

In preferred iterations, R[3], R[4], R[5], and R[6] are each hydrogen. R[1] is preferably alkyl, cycloalkyl, cycloalkylmethyl, allyl, or aryl; or more preferably methyl, ethyl, propyl, allyl, cyclopropylmethyl, cyclobutylmethyl, benzyl, or propargyl.

In an iteration of this embodiment, the compound comprising Formula (II) comprises Formula (IIa). For purposes of illustration, Reaction Scheme 2 depicts production of the compound comprising Formula (IIa) or a pharmaceutically acceptable salt thereof in accordance with one aspect of the

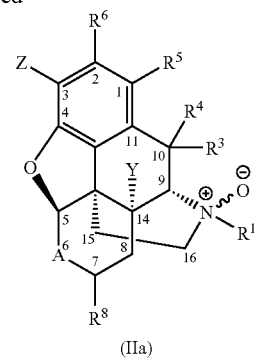

(IIa)

invention:

wherein:

A is selected from the group consisting of {—}C(O){—}, {—}C(=CH$_2$){—}, {—}CH$_2${—}, and {—}CH(A[1]){—}, wherein the carbons at positions 6 and 14 may be connected by an alkano bridge;

A[1] is selected from the group consisting of hydroxy, alkoxy, acyloxy, amido, hydrocarbyl, and substituted hydrocarbyl;

R[1] is selected from the group consisting of hydrocarbyl and substituted hydrocarbyl;

R[8] is selected from the group consisting of hydrogen, hydroxy, alkyl, substituted alkyl, alkoxy, hydrocarbyl, and substituted hydrocarbyl;

Y is selected from the group consisting of hydrogen, hydroxy, alkoxy, and acyloxy; and Z is selected from the group consisting of hydroxy, alkoxy, and acyloxy.

Representative compounds comprising Formula (IIa) or pharmaceutically acceptable salts thereof include N-oxides of (+)-dihydromorphine, (+)-dihydrocodeine, (+)-hydrocodone, (+)-hydromorphone, (+)-oxycodone, (+)-oxycodeinone, (+)-oxymorphone, (+)-oxymorphinone, (+)-naloxone, (+)-naltrexone, (+)-nalbuphine, (+)-nalfurafine, (+)-nalmefene, (+)-buprenorphine, and (+)-etorphine.

In another iteration of this embodiment, the compound comprising Formula (II) comprises Formula (IIb). For purposes of illustration, Reaction Scheme 3 depicts production of the compound comprising Formula (IIb) or a pharmaceutically acceptable salt thereof in accordance with one aspect of the Reaction Scheme 2

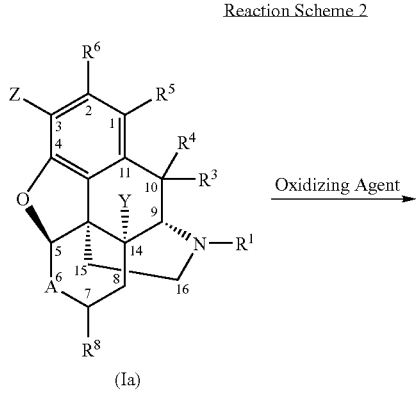

(Ia)

Reaction Scheme 3

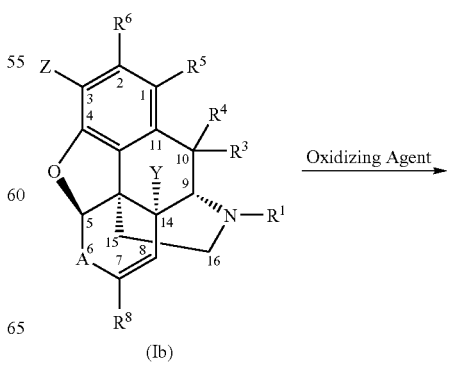

(Ib)

-continued

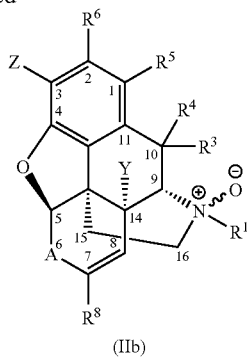

(IIb)

invention:
wherein:
A is selected from the group consisting of {—}C(O){—}, {—}C(=CH$_2$){—}, {—}CH$_2${—}, and {—}CH(A$^1$){—}; and
A$^1$, R$^1$, R$^8$, Y, and Z are as defined above for Reaction Scheme 2.

Representative compounds comprising Formula (IIb) or pharmaceutically acceptable salts thereof include N-oxides of (+)-morphine, (+)-codeine, and (+)-morphine-6-glucoronide.

In still another iteration of this embodiment, the compound comprising Formula (II) comprises Formula (IIc). For purposes of illustration, Reaction Scheme 4 depicts production of the compound comprising Formula (IIc) or a pharmaceutically acceptable salt thereof in accordance with one Reaction Scheme 4

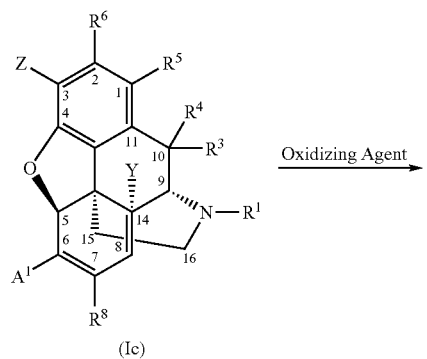

aspect of the invention:
wherein:
A$^1$, R$^1$, R$^8$, Y, and Z are as defined above for Reaction Scheme 2.

Representative compounds comprising Formula (IIc) or pharmaceutically acceptable salts thereof include N-oxides of (+)-thebaine and (+)-oripavine.

(b) Synthesis of Compounds Comprising Formula (IV)

In another embodiment of the invention, a (+)-morphinanium N-oxide compound comprising Formula (IV) or a pharmaceutically acceptable salt thereof is produced by reaction of a (+)-morphinan compound comprising Formula (III) or a pharmaceutically acceptable salt thereof with an oxidizing agent. For purposes of illustration, Reaction Scheme 5 depicts production of the compound comprising Formula (IV) or a pharmaceutically acceptable salt thereof in accordance with one aspect of the invention:

Reaction Scheme 5

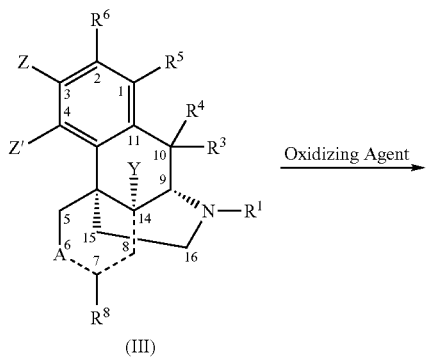

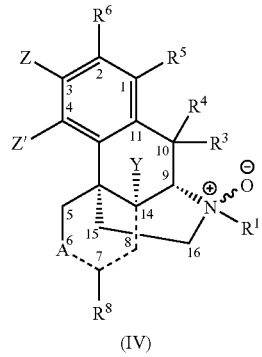

(IV)

wherein:
A is selected from the group consisting of {—}C(O){—}, {—}C(=CH$_2$){—}, {—}CH$_2${—}, {—}CH(A$^1$){—}, and
{—}C(A$^1$){=};
A$^1$ is selected from the group consisting of hydroxy, alkoxy, acyloxy, amido, hydrocarbyl, and substituted hydrocarbyl;
R$^1$ and R$^7$ are independently selected from the group consisting of hydrocarbyl and substituted hydrocarbyl;
R$^3$ and R$^4$ are independently selected from the group consisting of hydrogen, hydrocarbyl, and substituted hydrocarbyl;
R$^5$ and R$^6$ are independently selected from the group consisting of hydrogen, hydrocarbyl, substituted hydrocarbyl, halogen, {—}OH, and {—}OR$^7$;
R$^8$ is selected from the group consisting of hydrogen, hydrocarbyl, and substituted hydrocarbyl;
Y, if present, is selected from the group consisting of hydrogen, hydroxy, protected hydroxy, alkoxy, and acyloxy;

Z is selected from the group consisting of hydroxy, protected hydroxy, alkoxy, and acyloxy;

Z' is selected from the group consisting of hydrogen, hydroxy, protected hydroxy, alkoxy, and acyloxy; and the dashed lines between the carbon atoms at positions 6 and 7, 7 and 8, and 8 and 14 represent carbon to carbon bonds selected from the group consisting of (a) single bonds between all carbon atoms; (b) single bonds between the carbons at both positions 6 and 7 and 8 and 14, and a double bond between the carbons at positions 7 and 8; and (c) double bonds between the carbons at both positions 6 and 7 and 8 and 14, and a single bond between the carbons at positions 7 and 8, wherein Y is not present if there is a double bond between the carbons at positions 8 and 14.

As used herein, the term "substituted hydrocarbyl" refers to a hydrocarbyl moiety that is substituted with at least one heteroatom, including moieties in which a carbon chain atom is substituted with a heteroatom, provided that the heteroatom does not react with an oxidizing agent, as defined herein.

In preferred iterations, $R^3$, $R^4$, $R^5$, and $R^6$ are each hydrogen. $R^1$ is preferably alkyl, cycloalkyl, cycloalkylmethyl, allyl, or aryl; or more preferably methyl, ethyl, propyl, allyl, cyclopropylmethyl, cyclobutylmethyl, benzyl, or propargyl.

In an iteration of this embodiment, the compound comprising Formula (IV) comprises Formula (IVa). For purposes of illustration, Reaction Scheme 6 depicts production of the compound comprising Formula (IVa) or a pharmaceutically acceptable salt thereof in accordance with one aspect of

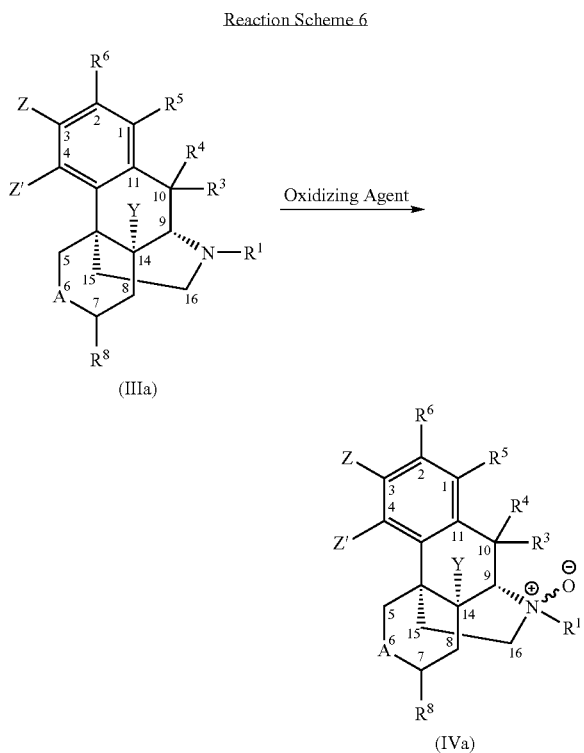

the invention:
wherein:
A is selected from the group consisting of {—}C(O){—}, {—}C(=CH$_2$){—}, {—}CH$_2${—}, and {—}CH(A$^1$){—};

$A^1$ is selected from the group consisting of hydroxy, alkoxy, acyloxy, amido, hydrocarbyl, and substituted hydrocarbyl;

$R^1$ is selected from the group consisting of hydrocarbyl and substituted hydrocarbyl;

$R^8$ is selected from the group consisting of hydrogen, hydroxy, alkyl, substituted alkyl, alkoxy, hydrocarbyl, and substituted hydrocarbyl;

Y is selected from the group consisting of hydrogen, hydroxy, protected hydroxy, alkoxy, and acyloxy;

Z is selected from the group consisting of hydroxy, protected hydroxy, alkoxy, and acyloxy; and Z' is selected from the group consisting of hydrogen, hydroxy, protected hydroxy, alkoxy, and acyloxy.

Representative compounds comprising Formula (IVa) or pharmaceutically acceptable salts thereof include N-oxides of (+)-dextrorphan, (+)-dextromethorphan, and (+)-dihydrosinomenine.

In another iteration of this embodiment, the compound comprising Formula (IV) comprises Formula (IVb). For purposes of illustration, Reaction Scheme 7 depicts production of the compound

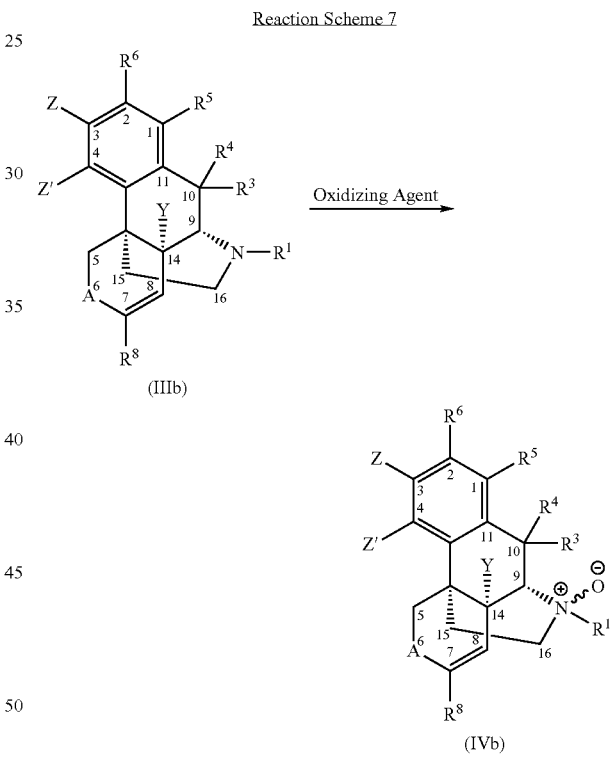

comprising Formula (IVb) or a pharmaceutically acceptable salt thereof in accordance with one aspect of the invention:
wherein:
A, $R^1$, $R^8$, Y, Z, and Z' are as defined above for Reaction Scheme 6.

Representative compounds comprising Formula (IVb) or pharmaceutically acceptable salts thereof include N-oxides of (+)-sinomenine.

In still another iteration of this embodiment, the compound comprising Formula (IV) comprises Formula (IVc). For purposes of illustration, Reaction Scheme 8 depicts production of the compound comprising Formula (IVc) or a pharmaceutically acceptable salt thereof in accordance with one aspect of the invention:

Reaction Scheme 8

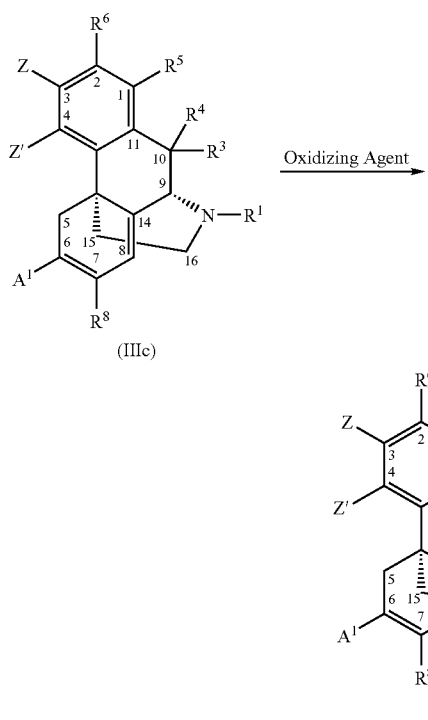

(IIIc)

(IVc)

wherein:
A¹, R¹, R⁸, Z, and Z' are as defined above for Reaction Scheme 6.

(c) Reaction Mixture

The process of the invention commences with formation of a reaction mixture by combining a compound comprising compound comprising Formulas (I) or (III) with an oxidizing agent. A variety of oxidizing agents are suitable for use in the process of the invention. Examples of oxidizing agents that may be used include, but are not limited to tungsten(VI) oxide, chromium oxide, dichromate, copper oxide, nickel oxide, cobalt oxide, silver oxide, oxides of mercury, oxides of lead, selenium oxide, ruthenium oxide, hydrogen peroxide, peroxysulfate, peroxyacetic acid, 3-chloroperoxybenzoic acid, $RCO_3H$, wherein R is selected from the group consisting of hydrogen, an alkyl, a substituted alkyl, an aryl, a substituted aryl, dichromates (e.g., ammonium dichromate, potassium dichromate, sodium dichromate, and the like); bromates (e.g., barium bromate, magnesium bromate, potassium bromate, sodium bromate, and the like); chlorates (e.g., ammonium chlorate, barium chlorate, calcium chlorate, potassium chlorate, sodium chlorate, and the like); chlorites (e.g., copper chlorite, lead chlorite, potassium chlorite, sodium chlorite, and the like); chloroisocyanuric acids (e.g., trichloroisocyanuric acid, and the like); chromates (e.g., potassium chromate, and the like); chromium oxides (e.g., chromic anhydride (chromium trioxide)); dichromates (e.g., sodium dichromate, potassium dichromate, and the like); hydrogen peroxide; hypobromites (e.g., sodium hypobromite, and the like); hypochlorites (e.g., calcium hypochlorite, potassium hypochlorite, sodium hypochlorite, and the like); hypoiodites (e.g., sodium hypoiodite, potassium hypoiodite, and the like); inorganic peroxides (e.g., barium peroxide, calcium peroxide, cesium peroxide, lithium peroxide, magnesium peroxide, potassium peroxide, rubidium peroxide, sodium peroxide, strontium peroxide, and the like); iodates (e.g., calcium iodate, potassium iodate, sodium iodate, zinc iodate, and the like); iodine oxides (e.g., diiodine pentaoxide, and the like); lead oxides (e.g., lead dioxde, and the like); manganese dioxide; nitrates (e.g., ammonium nitrate, ammonium cerium nitrate, barium nitrate, potassium nitrate, silver nitrate, sodium nitrate, and the like); nitric acid; nitrites (e.g., potassium nitrite, sodium nitrite, and the like); perchlorates (e.g., ammonium perchlorate, potassium perchlorate, sodium perchlorate, and the like); periodates (e.g., potassium periodate, sodium periodate, and the like); periodic acids (e.g., metaperiodic acid, and the like); permanganates (e.g., ammonium permanganate, magnesium permanganate, potassium permanganate, sodium permanganate, and the like); peroxoborates (e.g., ammonium peroxoborate, and the like); perchloric acid; peroxodisulfates (e.g., ammonium peroxodisulfates, potassium peroxydisulfate, and the like); peroxyacids (e.g., peroxyacetic acid, peroxybenzoic acid, peroxyformic acid, trifluoroperacetic acid, and the like); organic peroxides (e.g., benzoyl peroxide, and the like); tetroxides (e.g., osmium tetroxide, ruthenium tetroxide, and the like); dimethyldioxirane; and oxygen. As the oxygen source, air may also be used. In an exemplary embodiment the oxidizing agent is hydrogen peroxide.

The mole-to-mole ratio of the compound comprising Formulas (I) or (III) to oxidizing agent can and will vary. In general, the mole-to-mole ratio of the compound comprising Formulas (I) or (III) to the oxidizing agent may range from 1:1 to about 1:20. In some embodiments, the mole-to-mole ratio of the compound comprising Formulas (I) or (III) to the oxidizing agent may be about 1:1, 1:1.1, 1:1.5, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, or 1:20. In a preferred embodiment, the mole-to-mole ratio of the compound comprising Formulas (I) or (III) to the oxidizing agent may range from about 1:10 to about 1:15.

The reaction mixture, as detailed herein, generally also comprises a solvent. Those of skill in the art will appreciate that they solvent utilized will depend upon a variety of factors, including the chemical nature of the starting compound. In some embodiments, the solvent may be a protic solvent. Non-limiting suitable examples of protic solvents include, but are not limited to, methanol, ethanol, isopropanol, n-propanol, isobutanol, n-butanol, s-butanol, t-butanol, formic acid, acetic acid, water, and combinations thereof. In an exemplary embodiment, the protic solvent is methanol. In other embodiments, the solvent may be an aprotic solvent. Non-limiting examples of suitable aprotic solvents include acetone, acetonitrile, N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), N,N-dimethylacetamide (DMAC), N-methyl-2-pyrrolidinone (NMP), ethyl acetate, ethyl formate, ethyl methyl ketone, formamide, hexachloroacetone, hexamethylphosphoramide, methyl acetate, N-methylacetamide, N-methylformamide, methylene chloride, nitrobenzene, nitromethane, propionitrile, sulfolane, tetramethylurea, toluene, trichloromethane, xylenes, and combinations thereof. In still other embodiments, the solvent may be an organic solvent. Suitable organic solvents include, but are not limited to, alkane and substituted alkane solvents (including cycloalkanes), aromatic hydrocarbons, esters, ethers, combinations thereof, and the like. Specific organic solvents that may be employed, include, for example, acetonitrile, benzene, butyl acetate, t-butyl methylether, chlorobenzene, chloroform, chloromethane, cyclohexane, dichloromethane, dichloroethane, ethyl acetate, diethylene glycol, fluorobenzene, heptane, hexane, isopropyl acetate, pentyl acetate, n-propyl acetate, tetrahydrofuran, toluene, and combinations thereof. In additional embodiments, the solvent may comprise a mixture of protic, aprotic, and/or organic solvents as delineated above.

The amount of solvent in the reaction mixture may vary. Typically, the weight-to-weight ratio of solvent to the compound comprising Formulas (I) or (III) may range from about 2:1 to about 100:1, preferably from about 3:1 to about 30:1, or more preferably from about 5:1 to about 15:1. In some embodiments, the weight-to-weight ratio of solvent to the compound comprising Formulas (I) or (III) may be about 1:5, 1:6, 1:7, 1:8, 1:9, 1:10, 1:11, 1:12, 1:13, 1:14, or 1:15.

(d) Reaction Conditions

In general, the oxidation reaction may be conducted at a temperature that ranges from about −10° C. to about 120° C. for a period of time that is sufficient to convert a substantial portion of the compound comprising Formulas (I) or (III) to Formulas (II) or (IV), respectively. In one embodiment, the temperature of the reaction may range from about −10° C. to about 80° C. In another embodiment, the temperature may range from about −10° C. to about 50° C. In still another embodiment, the temperature of the reaction may range from about −5° C. to about 30° C. In a further embodiment, the temperature of the reaction may be about room temperature (~25° C.). The reaction is preferably performed under ambient pressures and preferably in an inert atmosphere (e.g., nitrogen or argon).

Typically, the reaction is allowed to proceed for a sufficient period of time until the reaction is complete, as determined by chromatography (e.g., TLC or HPLC). In this context, a "completed reaction" generally means that the reaction mixture contains a significantly diminished amount of compounds comprising Formula (I) or Formula (III) and a significantly increased amount of compounds comprising Formula (II) or Formula (IV), respectively, compared to the amounts of each present at the beginning of the reaction. Typically, the amount of compounds comprising Formula (I) or Formula (III) remaining in the reaction mixture may be less than about 5%, and preferably less than about 1%.

Upon completion of the reaction, the reaction mixture may be cooled to about 4° C. or less. Once the solution has cooled, filtration may be performed (for example by use of a celite plug) to remove impurities. The product may be isolated by phase extraction, liquid chromatography, crystallization, or other means familiar to those of skill in the art. The final product may washed and dried, and analyzed by HPLC, HPLC, MS, NMR, IR, or TGA. The yield of the compound comprising Formula (II) or Formula (IV) may vary. Typically, the yield of the compound may range from about 60% to about 99%, and more specifically from about 70% to about 80%.

DEFINITIONS

The compounds described herein may have asymmetric centers. Compounds of the present invention containing an asymmetrically substituted atom may be isolated in optically active or racemic form. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "acyl," as used herein alone or as part of another group, denotes the moiety formed by removal of the hydroxy group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic aromatic groups. These aromatic groups are preferably monocyclic, bicyclic, or tricyclic groups containing from 6 to 14 atoms in the ring portion. The term "aromatic" encompasses "aryl" groups defined below.

The term "aryl" or "Ar" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl is the preferred aryl.

The terms "halogen" or "halo" as used herein alone or as part of another group refer to chlorine, bromine, fluorine, and iodine.

The term "heteroatom" refers to atoms other than carbon and hydrogen. Examples of heteroatoms include oxygen, nitrogen, silicon, phosphorous, boron, sulfur, and halogen, provided that the heteroatom does not react with an oxidizing agent.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring, provided that the heteroatom does not react with an oxidizing agent. The heterocyclo group preferably has 1 or 2 oxygen atoms and/or 1 to 4 nitrogen atoms in the ring, and is bonded to the remainder of the molecule through a carbon or heteroatom.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The term "protecting group" as used herein denotes a group capable of protecting an oxygen atom, wherein the protecting group may be removed, subsequent to the reaction for which protection is employed, without disturbing the remainder of the molecule. Exemplary protecting groups include ethers (e.g., allyl, triphenylmethyl (trityl or Tr), p-methoxybenzyl (PMB), p-methoxyphenyl (PMP)), acetals (e.g., methoxymethyl (MOM), β-methoxyethoxymethyl (MEM), tetrahydropyranyl (THP), ethoxy ethyl (EE), methylthiomethyl (MTM), 2-methoxy-2-propyl (MOP), 2-trimethylsilylethoxymethyl (SEM)), esters (e.g., benzoate (Bz), allyl carbonate, 2,2,2-trichloroethyl carbonate (Trac), 2-trimethylsilylethyl carbonate), silyl ethers (e.g., trimethylsilyl (TMS), triethylsilyl (TES), triisopropylsilyl (TIPS), triphenylsilyl (TPS), t-butyldimethylsilyl (TBDMS), t-butyldiphenylsilyl (TBDPS) and the like. A variety of protecting groups and the synthesis thereof may be found in "Protective Groups in Organic Synthesis" by T. W. Greene and P. G. M. Wuts, John Wiley & Sons, 1999.

The "substituted hydrocarbyl" moieties described herein are hydrocarbyl moieties that are substituted with at least one heteroatom, including moieties in which a carbon chain atom is substituted with a heteroatom, provided that the heteroatom does not react with an oxidizing agent. Suitable substituents include halogen, heterocyclo, alkoxy, alkenoxy, aryloxy, hydroxy, protected hydroxy, acyl, acyloxy, nitro, amido, nitro, cyano, ketals, acetals, esters and ethers.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

Having described the invention in detail, it will be apparent that modifications and variations are possible without departing from the scope of the invention defined in the appended claims.

EXAMPLES

The following examples illustrate various iterations of the invention.

Example 1

Synthesis of (+)-Hydrocodone N-Oxide

The following scheme depicts the synthesis of (+)-hydrocodone N-oxide from (+)-hydrocodone.

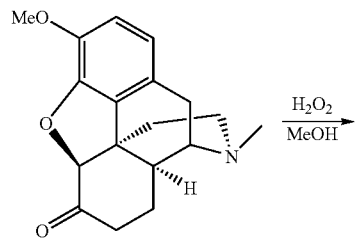

Chemical Formula: $C_{18}H_{21}NO_3$
Molecular Weight: 299.36

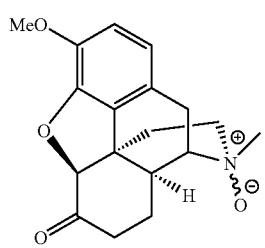

Chemical Formula: $C_{18}H_{21}NO_4$
Molecular Weight: 315.36

Hydrogen peroxide (2.5 mL, 50% w/v, 36.8 mmol, 11 eq.) was added drop-wise to a cooled solution of (+)-hydrocodone (1.0 g, 3.34 mmol, 1.0 eq.) in 10 mL of methanol (MeOH) in an ice bath. The reaction mixture was gradually warmed to room temperature overnight. High phase liquid chromatography (HPLC) analysis indicated the reaction was done. Approximately 50 mg $MnO_2$ was added to the reaction to decompose the excess hydrogen peroxide. Bubbling was observed after adding $MnO_2$. After the bubbling stopped, the reaction was filtered through celite and the solid residue was washed with methanol (3 mL×3). After removal of the volatiles from the combined filtrates on a rotoevaporator unit, a grey solid remained. The grey solid was added to 30 mL brine, the resulting suspension was cooled to approximately 0° C. in an ice bath, and the pH was adjusted to 1 with 6 N HCl. The product was extracted with dichloromethane (3×20 mL) and the combined organic phases were dried over anhydrous magnesium sulfate. After removing volatiles of the dried organic phase by means of the rotoevaporator, a white solid was left, 0.78 g, a yield of 74%, with purity=98.7%. Two peaks were observed on ultra pressure liquid chromatography (UPLC) analysis, the smaller peak had 5.17% ratio and the bigger peak had 94.83% ratio. Both peaks had M+1=316.3 and fragmentation pattern on LC-MS analysis.

Example 2

Synthesis of (+)-Hydrocodone N-Oxide and Isolation of Isomers

The following reaction scheme depicts the oxidation of (+)-hydrocodone to form (+)-hydrocodone N-oxide.

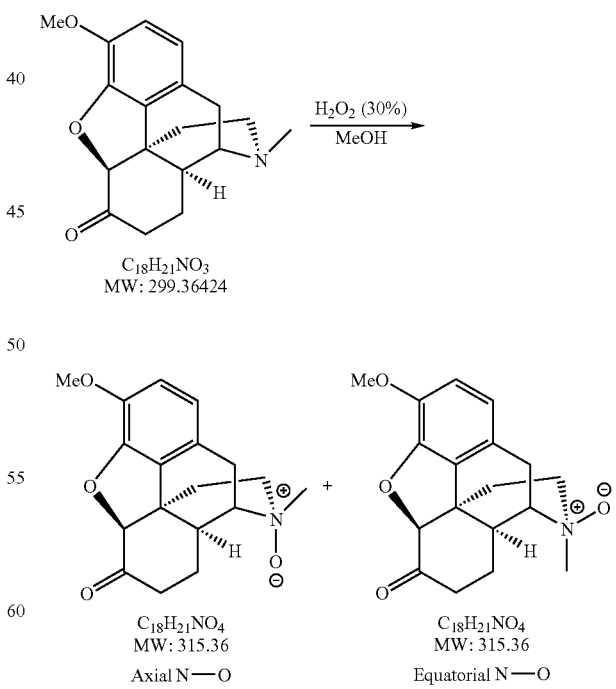

(+)-Hydrocodone N-oxide may be prepared in high yield by N-oxidation of (+)-hydrocodone base with hydrogen peroxide in the presence of a protic solvent. Accordingly, a suspension of 4.348 g (+)-hydrocodone base (14.52 mmol) in 50 mL of methanol may be slowly mixed with 19 mL of 30% hydrogen peroxide ($H_2O_2$) (186 mmol, 12.8 eq.) at room temperature. The suspension may be stirred overnight at room temperature under nitrogen. The completeness of the reaction may be monitored by TLC analysis (e.g., $CHCl_3$:MeOH:$NH_4OH$, 80:20:1). The starting material should be consumed and two products may be detected (major product, $R_f$ 0.44, and minor product, $R_f$ 0.25). The reaction mixture may be was cooled in an ice-water bath and the quenched with manganese dioxide ($MnO_2$). After filtration though a plug of celite followed by concentration, the crude reaction mixture may be subjected to flash column chromatography ($CHCl_3$:MeOH:$NH_4OH$ gradient, from 100:0:1 to 95:5:1) such that both products are isolated. By mass spectroscopy (MS) analysis, both major (3.7 g) and minor (230 mg) products have the same molecular weight and similar fragmentation patterns consistent for the N-oxide isomers. HPLC may be use to determine that both peaks (major at 6.65 min, minor at 4.37 min) are chromatographically pure. Nuclear magnetic resonance (NMR) may be used to show that the minor product could be a mixture of two or three compounds. NMR analysis may show that the major product is the (+) hydrocodone N-oxide with an axial N—O bond. The major isomer may be purified by flash column chromatography ($CHCl_3$:MeOH:$NH_4OH$ gradient, from 100:0:1 to 95:5:1) with four fractions being collected (F1, 97.55% area; F2, 98.05% area; F3, 97.51% area and F4, 98.19% area). Fractions 2 and 4 may be combined, and after removal of the solvent, 1.45 g of the major product may be obtained (C1, 98.36% area) as an off-white foam. Fractions 1 and 3 may be combined, and after solvent removal, 1.26 g of product may be obtained (C2) as an off-white foam. C1 may be further analyzed and verified by infrared spectroscopy (IR), thermogravimetric analysis (TGA), NMR, HPLC, and MS methods.

What is claimed is:

1. A compound of Formula (IV) or a pharmaceutically acceptable salt thereof:

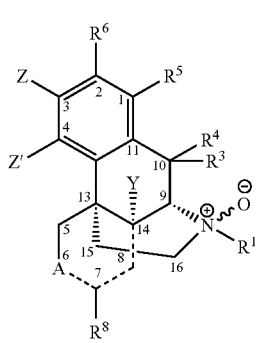

(IV)

wherein:

A is chosen from {—}C(O){—}, {—}C(=$CH_2$){—}, {—}($CH_2$){—}, {—}(CH($A^1$)){—}, and {—}C($A^1$){=};

$A^1$ is chosen from hydroxy, alkoxy, acyloxy, amido, hydrocarbyl, and substituted hydrocarbyl;

$R^1$ and $R^7$ are independently chosen from hydrocarbyl and substituted hydrocarbyl;

$R^3$ and $R^4$ are independently chosen from hydrogen, hydrocarbyl, and substituted hydrocarbyl;

$R^5$ and $R^6$ are independently chosen from hydrogen, hydrocarbyl, substituted hydrocarbyl, halogen, {—}OH, and {—}$OR^7$;

$R^8$ is chosen from hydrogen, hydrocarbyl, and substituted hydrocarbyl;

Y, if present, is chosen from hydrogen, hydroxy, protected hydroxy, alkoxy, and acyloxy;

Z is chosen from hydroxy, protected hydroxy, alkoxy, and acyloxy;

Z' is chosen from hydrogen, hydroxy, protected hydroxy, alkoxy, and acyloxy; and the dashed lines between the carbon atoms at positions 6 and 7, 7 and 8, and 8 and 14 represent carbon to carbon bonds selected from the group consisting of (a) single bonds between all carbon atoms; (b) single bonds between the carbons at both positions 6 and 7 and 8 and 14, and a double bond between the carbons at positions 7 and 8, wherein A is not {—}C(O){—} if there is a double bond between the carbons at positions 7 and 8; and (c) double bonds between the carbons at both positions 6 and 7 and 8 and 14, and a single bond between the carbons at positions 7 and 8, wherein Y is not present if there is a double bond between the carbons at positions 8 and 14.

2. The compound of claim 1, wherein the compound is Formula (IVa) or a pharmaceutically acceptable salt thereof:

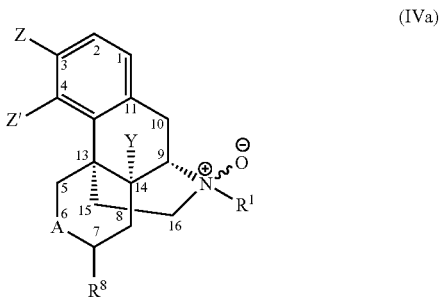

(IVa)

wherein:

A is chosen from {—}C(O){—}, {—}C(=$CH_2$){—}, {—}($CH_2$){—}, and {—}(CH($A^1$)){—};

$A^1$ is chosen from hydroxy, alkoxy, acyloxy, amido, hydrocarbyl, and substituted hydrocarbyl;

$R^1$ is chosen from hydrocarbyl and substituted hydrocarbyl;

$R^8$ is chosen from hydrogen, hydroxy, alkyl, substituted alkyl, alkoxy, hydrocarbyl, and substituted hydrocarbyl;

Y is chosen from hydrogen, hydroxy, protected hydroxy, alkoxy, and acyloxy;

Z is chosen from hydroxy, protected hydroxy, alkoxy, and acyloxy; and

Z' is chosen from hydrogen, hydroxy, protected hydroxy, alkoxy, and acyloxy.

3. The compound of claim 2, wherein the compound or the pharmaceutically acceptable salt thereof is an N-oxide of a compound chosen from (+)-dextrorphan, (+)-dextromethorphan and (+)-dihydrosinomenine.

4. The compound of claim 1, wherein the compound is Formula (IVb) or a pharmaceutically acceptable salt thereof:

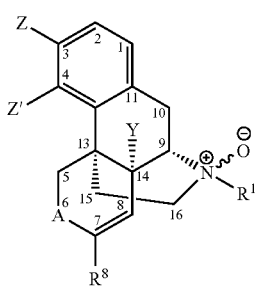

(IVb)

wherein:
- A is chosen from {—}C(=CH$_2$){—}, {—}(CH$_2$){—}, and {—}CH(A$^1$){—};
- A$^1$ is chosen from hydroxy, alkoxy, acyloxy, amido, hydrocarbyl, and substituted hydrocarbyl;
- R$^1$ is chosen from hydrocarbyl and substituted hydrocarbyl;
- R$^8$ is chosen from hydrogen, hydroxy, alkyl, substituted alkyl, alkoxy, hydrocarbyl, and substituted hydrocarbyl;
- Y is chosen from hydrogen, hydroxy, protected hydroxy, alkoxy, and acyloxy;
- Z is chosen from hydroxy, protected hydroxy, alkoxy, and acyloxy; and
- Z' is chosen from hydrogen, hydroxy, protected hydroxy, alkoxy, and acyloxy.

5. The compound of claim 1, wherein the compound is Formula (IVc) or a pharmaceutically acceptable salt thereof:

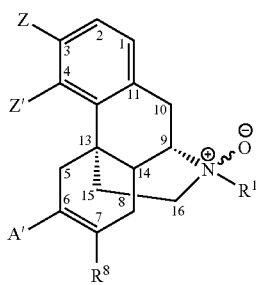

(IVc)

wherein:
- A$^1$ is chosen from hydrogen, hydroxy, alkoxy, acyloxy, amido, hydrocarbyl, and substituted hydrocarbyl;
- R$^1$ is chosen from hydrocarbyl and substituted hydrocarbyl;
- R$^8$ is chosen from hydrogen, hydroxy, alkyl, substituted alkyl, alkoxy, hydrocarbyl, and substituted hydrocarbyl;
- Z is chosen from hydroxy, protected hydroxy, alkoxy, and acyloxy; and
- Z' is chosen from hydrogen, hydroxy, protected hydroxy, alkoxy, and acyloxy.

6. A process for the preparation of a compound of claim 1, the process comprising contacting a (+)-morphinan comprising a tertiary amine at position 17 or a pharmaceutically acceptable salt thereof with an oxidizing agent to form the compound of claim 1, wherein the (+)-morphinan comprising a tertiary amine at position 17 is a compound of Formula (III) or a pharmaceutically acceptable salt thereof; the compound of claim 1 is a compound of Formula (IV) or a pharmaceutically acceptable salt thereof, and the process proceeds according to the following reaction:

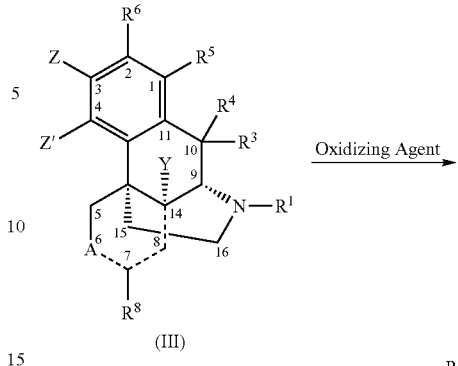

(III)

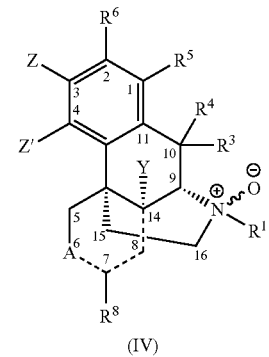

(IV)

wherein:
- A is chosen from {—}C(O){—}, {—}C(=CH$_2$){—}, {—}(CH$_2$){—}, {—}(CH(A$^1$)){—}, and {—}C(A$^1$){=};
- A$^1$ is chosen from hydroxy, alkoxy, acyloxy, amido, hydrocarbyl, and substituted hydrocarbyl;
- R$^1$ and R$^7$ are independently chosen from hydrocarbyl and substituted hydrocarbyl;
- R$^3$ and R$^4$ are independently chosen from hydrogen, hydrocarbyl, and substituted hydrocarbyl;
- R$^5$ and R$^6$ are independently chosen from hydrogen, hydrocarbyl, substituted hydrocarbyl, halogen, {—}OH, and {—}OR$^7$;
- R$^8$ is chosen from hydrogen, hydrocarbyl, and substituted hydrocarbyl;
- Y, if present, is chosen from hydrogen, hydroxy, protected hydroxy, alkoxy, and acyloxy;
- Z is chosen from hydroxy, protected hydroxy, alkoxy, and acyloxy;
- Z' is chosen from hydrogen, hydroxy, protected hydroxy, alkoxy, and acyloxy; and
- the dashed lines between the carbon atoms at positions 6 and 7, 7 and 8, and 8 and 14 represent carbon to carbon bonds selected from the group consisting of (a) single bonds between all carbon atoms; (b) single bonds between the carbons at both positions 6 and 7 and 8 and 14, and a double bond between the carbons at positions 7 and 8, wherein A is not {—}C(O){—} if there is a double bond between the carbons at positions 7 and 8; and (c) double bonds between the carbons at both positions 6 and 7 and 8 and 14, and a single bond between the carbons at positions 7 and 8, wherein Y is not present if there is a double bond between the carbons at positions 8 and 14.

7. The process of claim 6, wherein the oxidizing agent is chosen from a transition metal catalyst, hydrogen peroxide, peroxysulfate, peroxyacetic acid, 3-chloroperoxybenzoic acid, and RCO₃H, wherein R is chosen from hydrogen, an alkyl, a substituted alkyl, an aryl, a substituted aryl, and combinations thereof.

8. The process of claim 6, wherein the mole to mole ratio of (+)-morphinan to oxidizing agent is from about 1:1 to about 1:20 and the oxidation reaction is conducted at a temperature ranging from about −10° C. to about 80° C.

9. The process of claim 6, wherein $R^3$, $R^4$, $R^5$, and $R^6$ are hydrogen; the oxidizing agent is chosen from tungsten(VI) oxide, chromium oxide, dichromate, copper oxide, nickel oxide, cobalt oxide, silver oxide, oxides of mercury, oxides of lead, selenium oxide, ruthenium oxide, hydrogen peroxide, peroxysulfate, peroxyacetic acid, 3-chloroperoxybenzoic acid, and RCO₃H, wherein R is chosen from hydrogen, an alkyl, a substituted alkyl, an aryl, a substituted aryl, and combinations thereof; the mole to mole ratio of the compound comprising Formula (III) or the pharmaceutically acceptable salt thereof to oxidizing agent is from about 1:1 to about 1:20, and the nitrogen at position 17 of the compound comprising Formula (IV) or the pharmaceutically acceptable salt thereof comprises an R or an S configuration.

\* \* \* \* \*

UNITED STATES PATENT AND TRADEMARK OFFICE
CERTIFICATE OF CORRECTION

PATENT NO. : 8,563,727 B2
APPLICATION NO. : 12/710383
DATED : October 22, 2013
INVENTOR(S) : Gary L. Cantrell et al.

Page 1 of 1

It is certified that error appears in the above-identified patent and that said Letters Patent is hereby corrected as shown below:

In the Claims:

In claim 6, column 28, line 44, delete "R3" and insert therein --R8--.

Signed and Sealed this
Thirty-first Day of December, 2013

Margaret A. Focarino
*Commissioner for Patents of the United States Patent and Trademark Office*